US00PP36467P2

(12) United States Plant Patent
Schreurs

(10) Patent No.: US PP36,467 P2
(45) Date of Patent: Feb. 18, 2025

(54) ***GERBERA* PLANT NAMED 'GOS202117'**

(50) Latin Name: *Gerbera hybrida*
Varietal Denomination: GOS202117

(71) Applicant: PIET SCHREURS HOLDING B.V., De Kwakel (NL)

(72) Inventor: Petrus N. J. Schreurs, De Kwakel (NL)

(73) Assignee: PIET SCHREURS HOLDING B.V., De Kwakel (NL)

( * ) Notice: Subject to any disclaimer, the term of this patent is extended or adjusted under 35 U.S.C. 154(b) by 0 days.

(21) Appl. No.: 18/644,384

(22) Filed: Apr. 24, 2024

(51) Int. Cl.
*A01H 5/02* (2018.01)
*A01H 6/14* (2018.01)

(52) U.S. Cl.
USPC ..... Plt./357

(58) Field of Classification Search
USPC ..... Plt./357
See application file for complete search history.

*Primary Examiner* — Susan McCormick Ewoldt
*Assistant Examiner* — Zachariah Allan Kay
(74) *Attorney, Agent, or Firm* — C. Anne Whealy

(57) ABSTRACT

A new and distinct cultivar of *Gerbera* plant named 'GOS202117', characterized by its broadly upright and uniformly mounding plant habit; moderately vigorous to vigorous growth habit and moderate growth rate; dense and bushy appearance; numerous inflorescences with bright red-colored ray florets; upright and moderately strong peduncles; and good garden performance and relative tolerance to low temperatures.

2 Drawing Sheets

Figure 1:
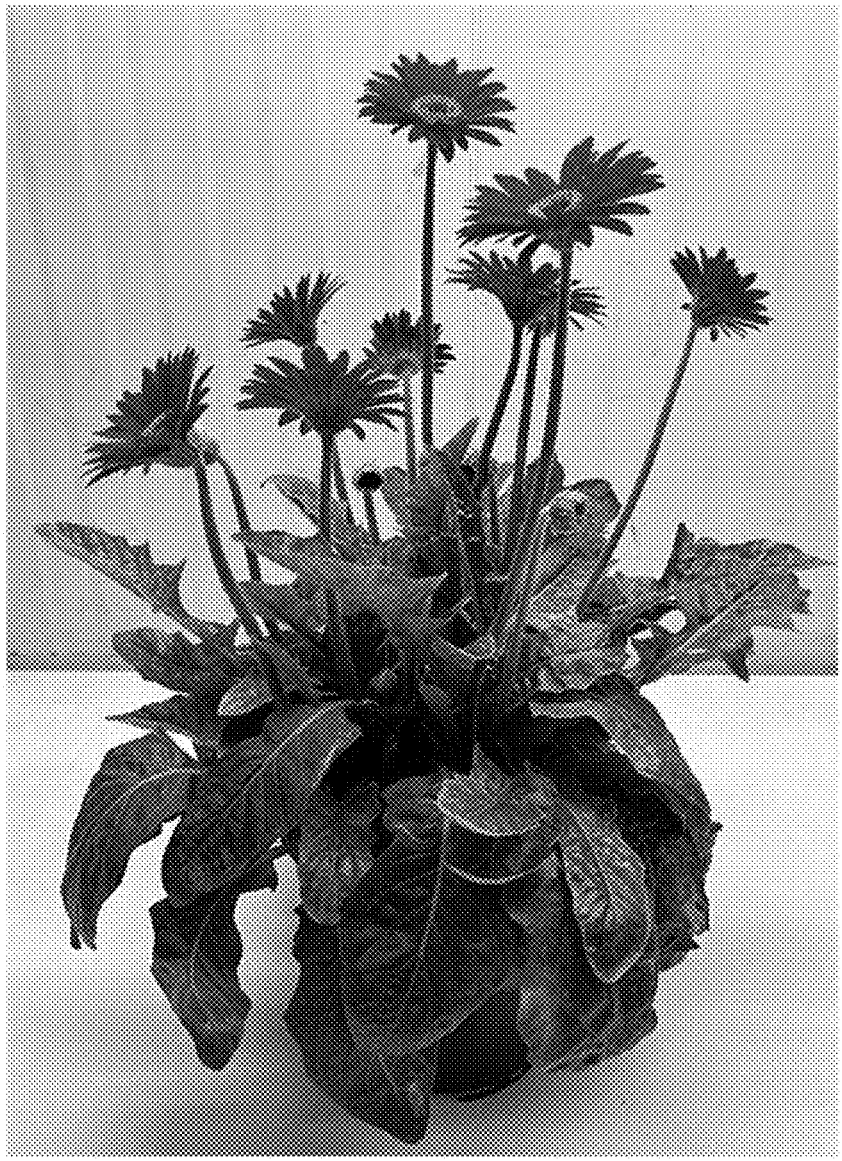

Botanical designation: *Gerbera hybrida.*
Cultivar denomination: 'GOS202117'.

BACKGROUND OF THE INVENTION

The present invention relates to a new and distinct cultivar of *Gerbera* plant, botanically known as *Gerbera hybrida* and hereinafter referred to by the cultivar name 'GOS202117'.

The new *Gerbera* plant is a product of a planned breeding program conducted by the Inventor in De Kwakel, The Netherlands. The objective of the breeding program is to create new garden *Gerbera* plants with numerous and attractive inflorescences, resistance to low temperatures and good garden performance.

The new *Gerbera* plant originated from a cross-pollination in October, 2020 of a proprietary selection of *Gerbera hybrida* identified as code number GO 1605, not patented, as the female, or seed, parent with a proprietary selection of *Gerbera hybrida* identified as code number GO 1222, not patented, as the male, or pollen, parent. The new *Gerbera* plant was discovered and selected as a single flowering plant from within the progeny of the stated cross-pollination in a controlled greenhouse environment in De Kwakel, The Netherlands in September, 2021.

Asexual reproduction of the new *Gerbera* plant by vegetative terminal cuttings since April, 2022 in a controlled environment in De Kwakel, The Netherlands, has shown that the unique features of this new *Gerbera* plant are stable and reproduced true to type in successive generations of asexual reproduction.

SUMMARY OF THE INVENTION

Plants of the new *Gerbera* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'GOS202117'. These characteristics in combination distinguish 'GOS202117' as a new and distinct *Gerbera* plant:

1. Broadly upright and uniformly mounding plant habit.
2. Dense and bushy appearance.
3. Numerous inflorescences with bright red-colored ray florets.
4. Upright peduncles.
5. Relative tolerance to low temperatures.

Plants of the new *Gerbera* differ primarily from plants of the female parent selection in the following characteristics:

1. Inflorescences of plants of the new *Gerbera* are single types whereas inflorescences of plants of the female parent selection are single to semi-double types.
2. Inflorescences of plants of the new *Gerbera* have a dark-colored disc whereas inflorescences of plants of the female parent selection do not have a dark-colored disc.

Plants of the new *Gerbera* differ primarily from plants of the male parent selection in the following characteristics:

1. Plants of the new *Gerbera* have narrower leaves than plants of the male parent selection.
2. Ray florets of plants of the new *Gerbera* are shorter than ray florets of plants of the male parent selection.

Plants of the new *Gerbera* can be compared to plants of the *Gerbera hybrida* 'Garswlove', disclosed in U.S. Plant Pat. No. 31,135. In side-by-side comparisons, plants of the new *Gerbera* differ from plants of 'Garswlove' in the following characteristics:

1. Plants of the new *Gerbera* have slightly smaller inflorescences than plants of 'Garswlove'.

2. Ray florets of plants of the new *Gerbera* are darker red in color than ray florets of plants of 'Garswlove'.
3. Inflorescences of plants of the new *Gerbera* have a dark-colored disc whereas inflorescences of plants of 'Garswlove' do not have a dark-colored disc.

BRIEF DESCRIPTION OF THE PHOTOGRAPHS

The accompanying photographs illustrate the overall appearance of the new *Gerbera* plant showing the colors as true as it is reasonably possible to obtain in colored reproductions of this type. Colors in the photographs may differ slightly from the color values cited in the detailed botanical description which accurately describe the colors of the new *Gerbera* plant.

The photograph on the first sheet (FIG. 1) is a side perspective view of a typical flowering plant of 'GOS202117' grown in a container.

Figure 2:
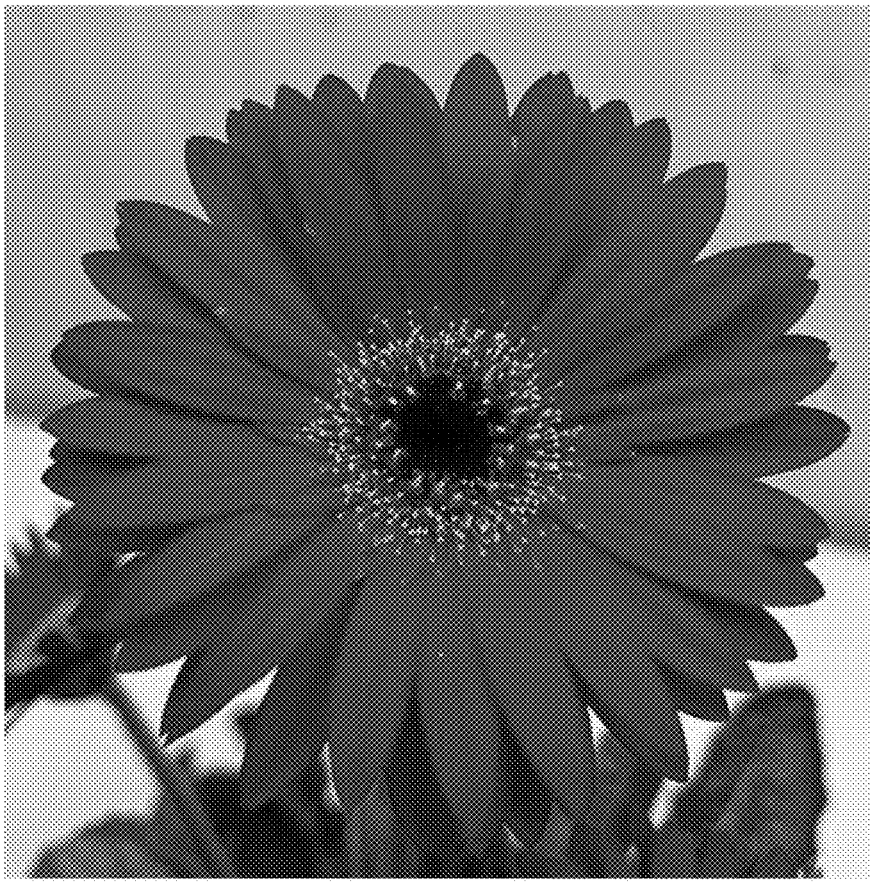

The photograph on the second sheet (FIG. 2) is a close-up view of a typical inflorescence of 'GOS202117'.

DETAILED BOTANICAL DESCRIPTION

The aforementioned photographs and following observations and measurements describe plants grown during the winter in 19-cm containers in a glass-covered greenhouse in De Kwakel, The Netherlands and under cultural practices typical of commercial garden *Gerbera* production. During the production of the plants, day temperatures ranged from 16° C. to 18° C. and night temperatures ranged from 10° C. to 11° C. Plants were five months old when the photographs and description were taken. In the following description, color references are made to The Royal Horticultural Society Colour Chart, 2015 Edition, except where general terms of ordinary dictionary significance are used.

Botanical classification: *Gerbera hybrida* 'GOS202117'.

Parentage:

*Female, or seed, parent*.—Proprietary selection of *Gerbera hybrida* identified as code number GO 1605, not patented.

*Male, or pollen, parent*.—Proprietary selection of *Gerbera hybrida* identified as code number GO 1222, not patented.

Propagation:

*Type*.—By vegetative cuttings.

*Time to initiate roots, summer*.—About 2.5 to 3 weeks at temperatures about 20° C. to 25° C.

*Time to initiate roots, winter*.—About 3 to 3.5 weeks at temperatures about 16° C. to 18° C.

*Time to produce a rooted young plant, summer*.—About four weeks at temperatures about 20° C. to 25° C.

*Time to produce a rooted young plant, winter*.—About five to six weeks at temperatures about 16° C. to 18° C.

*Root description*.—Fibrous; medium in thickness; typically white in color, actual color of the roots is dependent on substrate composition, water quality, fertilizer type and formulation, substrate temperature and physiological age of roots.

*Rooting habit*.—Freely branching; medium density.

Plant description:

*Appearance*.—Herbaceous perennial that is typically grown as a garden plant; broadly upright and uniformly mounding; roughly flattened globular in shape; numerous leaves arranged in basal rosettes; dense and bushy plant habit; inflorescences held above the foliar plane on erect and moderately strong basal peduncles; moderately vigorous to vigorous growth habit and moderate growth rate.

*Plant height, soil level to top of foliar plane*.—About 21.6 cm.

*Plant height, soil level to top of inflorescences*.—About 35.3 cm.

*Plant width or spread*.—About 41.9 cm.

Leaf description:

*Arrangement*.—Alternate, basal, simple.

*Length*.—About 21.4 cm.

*Width*.—About 8.4 cm.

*Shape*.—Oblanceolate to narrowly obovate in overall outline.

*Apex*.—Obtuse.

*Base*.—Broadly attenuate.

*Margin*.—Distally, entire; proximally, coarsely and irregularly angulate to runcinate; coarsely repand; sinuses parallel to divergent and shallow to deep.

*Texture and luster, upper surface*.—Mostly glabrous with main vein, sparsely pubescent; not rugose; slightly glossy.

*Texture and luster, lower surface*.—Moderately to densely pubescent; slightly rugose; slightly glossy to matte.

*Venation pattern*.—Pinnate.

*Color*.—Developing leaves, upper surface: Close to a blend of 137A and 143A. Developing leaves, lower surface: Close to a blend of 138A and 147B. Fully expanded leaves, upper surface: Close to NN137A; venation, close to 144A and 144B. Fully expanded leaves, lower surface: Close to 147B; venation, close to 144A and 144B.

*Petioles*.—Length: About 6.5 cm. Diameter: About 4 mm. Texture and luster, upper and lower surfaces: Moderately to densely pubescent; slightly glossy. Strength: Moderately strong to strong. Color, upper surface: Close to 146C; towards the margins, close to 148A; at the base, close to 183C. Color, lower surface: Close to 152D; towards the base, close to 176A.

Inflorescence description:

*Appearance*.—Composite single type inflorescence form with oblanceolate-shaped ray florets; solitary inflorescences borne on upright and moderately strong peduncles and held above the foliar plane; ray and disc florets arranged acropetally on a capitulum; inflorescences face mostly upright.

*Fragrance*.—None detected.

*Flowering season*.—Plants begin flowering about 1.5 months after planting; under garden conditions in The Netherlands, plants flower from late spring into the autumn; plants can be flowered year-round in the greenhouse.

*Inflorescence longevity*.—Depending on the temperature, inflorescences last about three to four weeks on the plant; inflorescences persistent.

*Quantity of inflorescences*.—Freely flowering habit with at least 13 developing and open inflorescences per plant at one time.

*Inflorescence buds*.—Height: About 2.2 cm. Diameter: About 2.2 cm. Shape: Flattened and broadly oblong. Texture and luster: Moderately to densely pubescent; matte. Color, immature involucral bracts: Close to 137D; towards the apex, close to 143B and 143C. Color, immature ray florets: Close to 3C strongly tinged with close to 32C.

*Inflorescence size*.—Diameter: About 8.1 cm. Depth (height): About 2.8 cm. Diameter of disc: About 3 cm.

*Receptacles*.—Height: About 3 mm. Diameter: About 5 mm. Shape: Broadly club-shaped to flattened rhomboidal. Color: Close to 157C and 157D.

*Ray florets*.—Quantity and arrangement: About 50 per inflorescence arranged in about three whorls. Orientation: About 80° from vertical; mostly horizontal; distally, slightly curved downward. Length: About 1.8 cm to 3.9 cm. Width: About 3 mm to 11 mm. Shape: Oblanceolate. Apex: Emarginate to acute. Base: Narrowly cuneate. Margin: Entire; not undulate. Texture and luster, upper surface: Smooth, glabrous; velvety; matte. Texture and luster, lower surface: Smooth, glabrous; slightly velvety; slightly glossy. Color: When opening, upper surface: Close to 35A; towards the base, close to 30A; towards the apex, close to 34A. When opening, lower surface: Close to 34D, blushed and striped with close to 22C. Fully opened, upper surface: Close to between 42A and 45B; color does not change with subsequent development. Fully opened, lower surface: Close to 31B, blushed and striped with close to 26B and 42B; color does not change with subsequent development.

*Disc florets*.—Quantity and arrangement: About 300 disc florets arranged at center of the inflorescence in an eight-whorl spiral; disc florets three-lobed with a central ray floret-like lobe and two narrower lateral lobes; lower 67% fused into a tube. Length, central lobe, fully mature: About 1.5 cm. Width, central lobe, fully mature: About 2 mm. Length, lateral lobs, fully mature: About 1.5 cm. Width, lateral lobes, fully mature: About 1 mm. Apex: Acute; recurved. Margin: Entire; not undulate. Texture, upper surface: Smooth, glabrous; moderately velvety; matte. Texture, lower surface: Smooth, glabrous; slightly velvety; slightly glossy. Color: When opening, upper and lower surfaces: Close to 45C; towards the base, close to 145D. Fully opened, upper and lower surfaces: Close to 44A; towards the base, close to 157D.

*Pappus*.—Quantity of hairs per floret: Numerous. Length: About 7 mm. Diameter: Fine, less than 1 mm. Texture and luster: Soft; matte. Color: Close to 11D.

*Phyllaries*.—Quantity and arrangement: About 60 per inflorescence arranged in about three whorls. Length: About 1.6 cm. Width (at base): About 2 mm. Shape: Linear. Apex: Narrowly acute. Base: Cuneate. Margin: Entire. Texture and luster, upper surface: Smooth, glabrous; moderately glossy. Texture and luster, lower surface: Moderately to densely pubescent; matte. Color, upper surface: Close to 144B and 145A; main vein, close to 143B; at the apex, close to 183A. Color, lower surface: Close to 137D; towards the apex, close to 143B and 143C; at the apex, close to 183A.

*Peduncles*.—Length: About 29.6 cm. Diameter: Proximally, about 6.5 mm and distally, about 4 mm. Strength: Moderately strong. Angle: About 10° from vertical. Texture and luster: Densely pubescent; slightly glossy. Color: Close to 152A, N199A and a blend of 152A and N199A.

*Reproductive organs*.—Androecium (present on disc florets only): Quantity per floret: Five. Filament length: About 1 cm. Filament color: Close to 157D. Anther shape: Linear; basifixed. Anther size: About 0.3 mm by 3 mm. Anther color: Close to 14A. Pollen amount: Scarce. Pollen color: Close to 10D. Gynoecium (present on ray and disc florets): Quantity per floret: One. Pistil length: About 1.1 cm. Stigma diameter: About 0.3 mm. Stigma shape: Cleft. Stigma color: Close to 56D. Style length: About 1 cm. Style color: Close to 51A; towards the base, close to 56D. Ovary color: Close to 157D.

*Seeds and fruits*.—To date, seed and fruit development has not been observed on plants of the new *Gerbera*.

Pathogen & pest resistance: To date, resistance to pathogens and pests common to *Gerbera* plants has not been observed on plants of the new *Gerbera* grown under commercial production conditions.

Garden performance: Plants of the new *Gerbera* have been observed to have good garden performance and to tolerate temperatures ranging from about −6° C. to about 35° C. and to be cold hardy to USDA Hardiness Zone 9.

It is claimed:

1. A new and distinct *Gerbera* plant named 'GOS202117' as illustrated and described herein.

* * * * *